United States Patent [19]

Workman, Jr.

[11] 4,195,072

[45] Mar. 25, 1980

[54] STABILIZED PLATELET FACTOR 4 IMMUNOASSAY STANDARDS

[75] Inventor: Erwin F. Workman, Jr., Vernon Hills, Ill.

[73] Assignee: Abbott Laboratories, North Chicago, Ill.

[21] Appl. No.: 922,135

[22] Filed: Jul. 5, 1978

[51] Int. Cl.$^2$ ............... G01N 33/16; A61K 43/00
[52] U.S. Cl. ............................. 424/1; 23/230 B; 252/408; 424/12
[58] Field of Search ............... 424/1, 12; 23/230 B; 252/408

[56] References Cited

PUBLICATIONS

Handen et al., J. Biol. Chem., 251, (1976), pp. 4273–4282.
Levine et al., Thrombosis, Res., 11, (1977), pp. 673–686.
Bolton et al., Thrombosis, Res., 8, (1976), pp. 51–58.

*Primary Examiner*—Benjamin R. Padgett
*Assistant Examiner*—Christine M. Nucker
*Attorney, Agent, or Firm*—John J. McDonnell

[57] ABSTRACT

The present invention encompasses a stabilized platelet factor 4 immunoassay standard comprising an aqueous solution containing 10 to 100 ng/ml of platelet factor 4, carrier protein, and an effective stabilizing amount of heparin, as well as $^{125}$I labeled platelet factor 4 reagent stabilized in the same manner. These reagents are useful for testing blood plasma for activation of the coagulation system.

5 Claims, No Drawings

STABILIZED PLATELET FACTOR 4 IMMUNOASSAY STANDARDS

BACKGROUND OF THE INVENTION

Platelet Factor 4 (PF4) is a small molecular weight protein that is secreted from the α-granules of platelets when the cells undergo the release reaction. This phenomenon occurs when the platelets become activated subsequent to contact with subendothelial tissue and a variety of other phsyiological agents including thrombin, ADP and epinephrine. Platelet factor 4 is quantitated using classical radioimmunoassay techniques, Thrombosis Research 8, pg 51–58, (1976) and Thrombosis Research 11, pg 673–686, (1977).

Platelet factor 4 (PF4) whether radiolabeled or not, will bind to specific antiserum. In a mixture of labeled and unlabeled ($^{125}$I-PF4 and PF4) protein, each will be bound to a limited amount of antiserum in proportion to its concentration in the mixture. When PF4 from plasma, serum or a standard solution is equilibrated with $^{125}$I-PF4 and PF4 antiserum, the amount of $^{125}$I-PF4 that is bound to the antiserum will be inversely proportional to the amount of nonradioactive PF4 present in the sample or standard solution. By separating the antiserum complex from unbound PF4 and measuring the radioactivity of $^{125}$I-PF4 bound in the complex, concentrations of added PF4 can be plotted versus % of $^{125}$I-PF4 bound. A standard curve can then be used to determine the amount of PF4 in the patient samples.

Stable standard samples are essential for reliable quantitation of platelet factor 4. Unexpectedly, it has been found that heparin, Merck Index, 9th Ed., 4510, stabilizes platelet factor 4 standard samples and labeled reagent. Heparin is a highly sulfated dextrorotatory mucopolysaccharide having specific anticoagulant properties. It is composed of D-glucosamine and D-glucuronic acid residues and has a molecular weight of about 20,000. Heparinic acid, physiologically acceptable alkaline metal and alkaline earth cationic salts such as sodium, potassium, lithium, magnesium, calcium or ammonium and the like, as well as other sulfated polysaccharides such as sulfated pectins and dextrins having heparin like activity are suitable sources for heparin activity for practicing the present invention.

Platelet factor 4 is a platelet specific protein with heparin neutralizing activity which is liberated during the platelet release reaction as measured by heparin thrombin clotting time test, Thrombosis Research 8, pg. 51–58, (1976).

BRIEF DESCRIPTION OF THE INVENTION

The present invention encompasses a stabilized platelet factor 4 immunoassay standard comprising an aqueous solution containing 10 to 100 ng/ml of platelet factor 4, carrier protein, and an effective stabilizing amount of heparin. A similarly stabilized reagent wherein the platelet factor 4 is labeled with $^{125}$I as well as test kits and methods for using these reagents.

DETAILED DESCRIPTION OF THE INVENTION

A set of standards corresponding to physiological concentrations of platelet factor 4, 0–100 ng/ml, for example, 0, 10, 30, 50, 100 ng/ml. These standards contain a carrier protein to aid in separation of antibody-antigen precipitation and to reduce the amount of platelet factor 4 adhered to the side of reagent and test viles. A portion of carrier protein coprecipitates with labeled and unlabeled platelet factor 4, which is bound to antibody in the antiserum.

Aqueous solutions are preferably buffered at physiologically compatible pH, a range of about 5–10. For example, 0.01 M Tris buffer in 0.15 M sodium chloride, pH about 8.2 is a preferred dilution buffer.

Carrier protein, 0.05–2.0 percent (weight/volume) about half albumin and half gamma globulin is an effective amount of carrier protein to effect efficient antigen-antibody precipitation and reduce adherence of test sample to walls of sample tubes. A preferred amount of carrier protein is about 0.2% bovine serum albumin and 1.5 mg/ml of bovine gamma globulin.

An antibacterial preservative such as sodium azide or thimerosal is desirable to prevent the growth of bacteria within the standard solution. 0.02% sodium azide is a preferred effective amount of antibacterial preservative. Those skilled in reagent and immunoassay arts will recognize interchangeability of buffers, proteins, preservatives and the variation of quantities to obtain suitable dilution buffer and effective amounts of carrier protein and effective amounts of antibacterial preservatives.

An effective stabilizing amount of heparin is about 3 to $10^{-5}$ units of heparin activity per ng platelet factor 4. The preferred amount is about $10^{-1}$ to $10^{-2}$ units/ng. In any event, there should be at least about $10^{-5}$ units/ng. One unit of heparin activity per milliliter of buffered diluent each containing 10, 30, 50 and 100 ng, respectively, of platelet factor 4 provides a highly effective set of standards. A typical sodium heparin preparation contains about 170 units/mg. U.S.P. Pharmacapia—Definition of 1 unit of Heparin—1 unit of heparin is that amount which when dissolved in 0.8 ml saline and added to 1 ml of recalcified sheep plasma (0.2 ml calcium chloride solution, 10 g/l) will cause the mixture to remain fluid for at least one hour.

The present invention also encompasses a $^{125}$I labeled reagent in aqueous solution having an antibacterial preservative, carrier protein as well as an effective stabilizing amount of heparin wherein the radioactivity is generally less than 0.5μ Ci/ml preferably in the range of 0.2–0.45μ Ci/ml as an effective amount of radioactivity for detection.

The heparin reagents of this present invention are conveniently combined in an assay kit for determining platelet factor 4. The following examples illustrate the present invention and are not intended to limit it in spirit or scope.

EXAMPLE I

Blood samples are obtained by standard venipuncture techniques, cooled and centrifuged. The plasma is drawn and 50μ l are placed in test tubes identified as unknown samples.

50μ l of standard having 0, 10, 30, 50 and 100 ng/ml of platelet factor 4 in 0.01 M Tris buffer (2-amino-2-hydroxymethyl-1,3-propanediol HCl) in 0.15 M sodium chloride having 1.5 mg/ml of boving gamma globulin, 0.2% bovine serum albumin, 1μ/ml of sodium heparin and 0.02% of sodium azide are placed in test tubes identified as standard samples.

300μ l of dilution buffer is pipetted into test tubes identified as non-specific binding samples.

All of the above samples receive 250μ l of $^{125}$I labeled platelet factor 4 solution having 0.45μ Ci or less/ml of radioactivity in 0.01 M Tris buffer with 0.15 M sodium chloride containing 0.2% bovine serum albumin, 1.5 mg/ml of bovine gamma globulin, 2.2 U/ml of sodium heparin, and 0.02% sodium azide.

The unknowns and standards then receive 250μ 1 of goat platelet factor 4 antiserum in 0.01 M Tris buffer in 0.15 M sodium chloride containing 0.2% bovine serum albumin, 1.5 mg/ml bovine gamma globulin and 0.02% sodium azide.

Total count tubes are prepared by pipetting 250μ l of $^{125}$I labeled platelet factor 4 in separate tubes.

The tubes are incubated at 22°-25° C. for about two hours.

Each tube except the total count tube (TCT) receives 1 ml of ammonium sulfate (73% saturated). The tubes are then mixed, centrifuged 1000 xg for 20 minutes, the supernatant decanted, and the radioactivity in the ammonium sulfate protein precipitate is measured in a scintillation well counter.

RESULTS

1. Calculate the percentage of $^{125}$I-PF4 bound to antiserum in the ammonium sulfate precipitate.

$$\frac{\text{cpm Standard}}{\text{cpm } TCT} \times 100 = \% \text{ Bound for Standard}$$

$$\frac{\text{cpm Unknown}}{\text{cpm } TCT} \times 100 = \% \text{ Bound for Unknown}$$

2. Plot the average % Bound for each PF4 standard on the vertical (Y) axis vs. the corresponding label concentration from each vial on the horizontal (X) axis. Using the five points, draw the best fit smooth curve. 3. To determine the concentration of PF4 in unknown samples, extend a horizontal line from the calculated % Bound found on the Y axis to the curve. At the point of intersection, extend a vertical line to the X axis and read the corresponding PF4 value for the unknown.

| PF4 RIA TYPICAL STANDARD CURVE | |
|---|---|
| Standard | Bound/Total |
| 0ng/ml | 50.28 |
| 10ng/ml | 39.66 |
| 30ng/ml | 28.53 |
| 50ng/ml | 23.90 |
| 100ng/ml | 19.18 |

Typical clinical results are:
Normal: less than 10ng/ml in plastma

Myocardial infarction
Coronary artery disease
Disseminated intravascular coagulation
Prosthetic heart valves
} Elevated levels sometimes exceeding 100ng

EXAMPLE II

Standards which are identical in all respects except one group contain 1 U/ml of heparin. (+) Heparin and the others without heparin (−) were tested over a six week period.

RESULTS

| | 50% Intercept ng/ml | |
|---|---|---|
| Time (Weeks) | (−) Heparin | (−) Heparin |
| 0 | 26 | 32 |
| 1 | 23 | 32 |
| 2 | 26 | 42 |
| 3 | 24 | 42 |
| 4 | 30 | 51 |
| 5 | 30 | 43 |
| 6 | 24 | 47 |

The 50% intercept remains reasonably constant when heparin is present, but increases in the control where no heparin is added. This increase in 50% intercept indicates a decrease in sensitivity and an apparent change in PF4 concentration of the standards.

What is claimed is:

1. A stabilized platelet factor 4 immunoassay standard comprising an aqueous solution containing 10 to 100 ng/ml of platelet factor 4, carrier protein and an effective stabilizing amount of heparin activity.

2. A stabilized platelet factor 4 immunoassay standard comprising a buffered diluent containing 10 to 100 ng/ml of platelet factor 4, carrier protein, an effective antibacterial amount of preservative and an effective stabilizing amount of heparin activity.

3. A stabilized $^{125}$I labeled platelet factor 4 immunoassay reagent comprising an aqueous solution containing $^{125}$I labeled platelet factor 4 having up to 0.45μ Ci/ml of radioactivity, carrier protein and an effective stabilizing amount of heparin activity.

4. A stabilized $^{125}$I labeled platelet factor 4 immunoassay reagent comprising a buffered diluent containing $^{125}$I labeled platelet factor 4 having up to 0.45μ Ci/ml of radioactivity, carrier protein, an effective antibacterial amount of preservative and an effective stabilizing amount of heparin activity.

5. In a radioimmunoassay method for platelet factor 4 in blood plasma wherein concentrations of platelet factor 4 in standards are used to derive concentrations of platelet factor 4 in blood plasma by competitive binding of $^{125}$I labeled platelet factor 4 and platelet factor 4 from test samples with platelet factor 4 antiserum, followed by precipitation and counting of bound $^{125}$I labeled platelet factor 4, the improvement comprising using heparin stabilized platelet factor 4 standards and heparin stabilized $^{125}$I labeled platelet factor 4.

* * * * *